(12) United States Patent
Greaves

(10) Patent No.: US 10,201,492 B2
(45) Date of Patent: Feb. 12, 2019

(54) COSMETIC PROCESS FOR ATTENUATING WRINKLES

(71) Applicant: L'OREAL, Paris (FR)

(72) Inventor: Andrew Greaves, Magny-le-Hongre (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/515,220

(22) PCT Filed: Sep. 29, 2015

(86) PCT No.: PCT/EP2015/072470
§ 371 (c)(1),
(2) Date: Mar. 29, 2017

(87) PCT Pub. No.: WO2016/050793
PCT Pub. Date: Apr. 7, 2016

(65) Prior Publication Data
US 2017/0209360 A1 Jul. 27, 2017

(30) Foreign Application Priority Data

Sep. 30, 2014 (FR) ..................................... 14 59266

(51) Int. Cl.
*A61K 8/91* (2006.01)
*A61K 8/31* (2006.01)
*A61Q 19/08* (2006.01)

(52) U.S. Cl.
CPC .................. *A61K 8/91* (2013.01); *A61K 8/31* (2013.01); *A61Q 19/08* (2013.01); *A61K 2800/82* (2013.01); *A61K 2800/882* (2013.01)

(58) Field of Classification Search
None
See application file for complete search history.

(56) References Cited

U.S. PATENT DOCUMENTS 5,871,573 A * 2/1999 Cook ..................... A61K 8/731
106/162.7
2006/0140895 A1 6/2006 Zheng et al.
2008/0181953 A1 7/2008 Cassin
2009/0118423 A1 * 5/2009 Kumar ................ C08B 37/0072
524/850
2012/0029089 A1 2/2012 Chu et al.

FOREIGN PATENT DOCUMENTS

FR 2 838 345 A1 10/2003

OTHER PUBLICATIONS

Kim Sin-Hee et al: "Synthesis and characterization of dextran-methacrylate hydrogels and structural study by SEM", Journal of Biomedical Materials Research, Wiley, New York, NY, US, vol. 49, No. 4, Jan. 1, 2000 (Jan. 1, 2000), pp. 517-527, XP002368945.
Smeds K A et al: "Photocrosslinkable Polysaccharides for in Situ Hydrogel Formation", Journal of Biomedical Materials Research, Wiley,New York, NY, US, vol. 54, No. 1, Jan. 1, 2001 (Jan. 1, 2001), pp. 115-121, XP008018719.
Burdick Jason A et al: "Controlled Degradation and Mechanical Behavior of Photopolymerized Hyaluronic Acid Networks", Biomacromolecules, American Chemical Society, US, vol. 6, Jan. 1, 2005 (Jan. 1, 2005), pp. 386-391, XP008069736.

* cited by examiner

*Primary Examiner* — Brian Gulledge
(74) *Attorney, Agent, or Firm* — Polsinelli PC

(57) ABSTRACT

The invention relates to a cosmetic process for caring for the skin, more particularly facial skin, in particular wrinkled skin, comprising:

(i) a step consisting in applying to the skin a composition, in particular a cosmetic composition, comprising, in a physiologically acceptable medium, a polysaccharide polymer grafted with (meth)acrylate groups and a photoactive compound, (ii) followed by a step consisting in exposing the skin to light radiation, preferably for at least 5 seconds.

The invention also relates to a composition comprising, in a physiologically acceptable medium, a polysaccharide polymer grafted with (meth)acrylate groups and a photoactive compound.

19 Claims, No Drawings

COSMETIC PROCESS FOR ATTENUATING WRINKLES

CROSS REFERENCE TO RELATED APPLICATIONS

This application is a National Phase filing under 35 U.S.C. § 371 of PCT/EP2015/072470 filed on Sep. 29, 2015; and this application claims priority to application Ser. No. 1459266 filed in France on Sep. 30, 2014 under 35 U.S.C. § 119. The entire contents of each application are hereby incorporated by reference.

The present invention relates to a process for attenuating wrinkles on the skin, using a composition comprising a (meth)acrylate-grafted polysaccharide polymer and a photoactive compound, and exposure of the treated skin to light.

During the ageing process, various signs appear on the skin, which are very characteristic of this ageing, resulting in particular in a modification of skin structure and functions. The main clinical signs of skin ageing are in particular the appearance of fine lines and deep wrinkles, which increase with age.

It is known practice to treat these signs of ageing using cosmetic or dermatological compositions containing active agents capable of combating ageing, such as α-hydroxy acids, β-hydroxy acids and retinoids. These active agents act on wrinkles by eliminating dead skin cells and by accelerating the cell renewal process. However, these active agents have the drawback of only being effective for the treatment of wrinkles after a certain application time. However, it is increasingly sought to obtain an immediate effect of the active agents used, rapidly resulting in smoothing out of wrinkles and fine lines and in the disappearance of the signs of fatigue.

Polymers of hyaluronic acid grafted with (meth)acrylate groups are described in document WO 2007/106738 and the publications J. Burdick et al "Controlled degradation and mechanical behavior photopolymerized hyaluronic acid networks", Biomacromolecules, 2005, 6, pages 386-391; Mark Grinstaff "Photocrosslinkable polysaccharides for in situ hydrogel formation", Journal of biomedical materials research, 2001, volume 55, Issue 2, pages 115-121. They are used to form hydrogels after crosslinking.

Dextran polymers grafted with methacrylate groups are described in document WO 2010/083039. They are used in combination with riboflavin and arginine or chitosan for forming, after crosslinking under UV exposure or exposure to visible light, hydrogels which are applied to the skin.

The article S. H. Kim, "Synthesis and characterization of dextran-methacrylate hydrogels and structural study by SEM" J. Biomed Mater Res, 49 (2005) 517 describes hydrogels obtained by photo-crosslinking after UV-exposure of dextran methacrylate.

Carrageenan is known for its skin tensioning properties, in particular in document FR-A-2838343.

The inventors have discovered that the application to the skin of a polysaccharide polymer grafted with (meth)acrylate groups combined with a photoactive compound, with the treated skin being exposed to light radiation, has an improved tensioning effect on the skin and thus makes it possible to immediately attenuate wrinkles on the skin. This tensioning effect also exhibits good water resistance, and therefore good persistence with respect to water.

More specifically, a subject of the present invention is a process, in particular a cosmetic process, for caring for the skin, more particularly facial skin, in particular wrinkled skin, comprising:

(i) a step consisting in applying to the skin a composition, in particular a cosmetic composition, comprising, in a physiologically acceptable medium, a polysaccharide polymer grafted with (meth)acrylate groups and a photoactive compound (photoinitiator),
(ii) followed by a step consisting in exposing the skin to light radiation, preferably for at least 5 seconds. This step can be repeated several times during the day.

The process according to the invention is in particular intended for smoothing out human facial and/or body skin and/or for decreasing or effacing the signs of skin ageing, in particular for reducing or effacing wrinkles and/or fine lines on the skin.

A subject of the invention is also a composition comprising, in a physiologically acceptable medium, a (meth)acrylate-grafted polysaccharide polymer and a photoactive compound, as previously described.

A subject of the invention is also a kit comprising a first composition, which is in particular a cosmetic composition, comprising said (meth)acrylate-grafted polysaccharide polymer as previously described and a second composition comprising a photoactive compound as previously described, the first and second compositions each being packaged in a distinct packaging assembly.

The composition packaging assembly is, in a known manner, any packaging that is suitable for storing cosmetic compositions (in particular a bottle, tube, spray bottle or aerosol bottle).

Such a kit allows the skin treatment process according to the invention to be performed.

The term "tensioning agent" is intended to mean compounds capable of having a noticeable tensioning effect, i.e. of smoothing out the skin and immediately reducing, or even causing to disappear, the wrinkles and fine lines.

The tensioning effect may be characterized by means of an in vitro retraction test as described in Example 1.

The term "polysaccharide grafted with (meth)acrylate groups" is intended to mean a polysaccharide of which all or some free hydroxyl groups have been esterified so as to form (meth)acrylate ester groups.

The grafted polysaccharide used according to the invention may be chosen from (meth)acrylate-grafted hyaluronic acid, (meth)acrylate-grafted dextran and (meth)acrylate-grafted carrageenan, such as those described hereinafter.

Advantageously, the (meth)acrylate-grafted polysaccharide has a weight-average molecular weight ranging from 5000 to 1 000 000 daltons, preferably ranging from 10 000 to 500 000 daltons, and even more preferentially ranging from 15 000 to 350 000 daltons.

According to a first embodiment of the process according to the invention, the grafted polysaccharide may be a (meth)acrylate-grafted hyaluronic acid.

Hyaluronic acid is a linear glycosaminoglycan composed of repeating D-glucuronic acid and N-acetyl-D-glucosamine units linked together via alternating beta-1,4 and beta-1,3 glycosidic linkages.

Preferably, the grafted hyaluronic acid polymer has a weight-average molecular weight ranging from 5000 to 1 000 000 daltons, more preferentially ranging from 10 000 to 500 000 daltons, and even more preferentially ranging from 15 000 to 350 000 daltons. The molecular weight can be determined in particular by liquid chromatography, the eluent being 0.1 M sodium chloride and 330 mg/l of sodium azide in water, with dextran as standard, and Wyatt Optilab T-Rex refractometer and Wyatt Dawn-Heleos II light scattering detectors.

Advantageously, the grafted hyaluronic acid polymer has a degree of grafting with (meth)acrylate groups ranging from 10% to 80% or 20% to 80%, preferably ranging from 40% to 70%, and preferentially ranging from 45% to 65%. The degree of grafting corresponds to the mole percentage of hydroxyl groups of the hyaluronic acid which are grafted with a (meth)acrylate group.

By way of example, a degree of grafting of 50% corresponds to 2 acrylate groups grafted onto the 4 hydroxyls of the repeating unit of the hyaluronic acid.

The grafting of hyaluronic acid with (meth)acrylate groups results from the presence of a (meth)acrylate ester group formed with the free hydroxyls of hyaluronic acid.

Preferably, the hyaluronic acid is grafted with acrylate groups.

The hyaluronic acid grafted with (meth)acrylate groups can be obtained by reaction of the hyaluronic acid with (meth)acrylic anhydride. The reaction is advantageously carried out in a basic aqueous medium, in particular in the presence of an organic or inorganic base such as, for example, sodium hydroxide. Preferably, the reaction is carried out at a temperature ranging from 5 to 10° C., in particular for a period of time ranging from 24 hours to 48 hours.

Advantageously, the grafted dextran polymer has a degree of grafting with (meth)acrylate groups ranging from 2% to 70%, preferably ranging from 3% to 65%, and preferentially ranging from 5% to 60%. The degree of grafting corresponds to the mole percentage of hydroxyl groups of the dextran which are grafted with a (meth)acrylate group.

By way of example, a degree of grafting of 50% corresponds to 1.5 acrylate groups grafted onto the 3 hydroxyls of the repeating unit of the dextran.

The grafting of dextran with (meth)acrylate groups results from the presence of a (meth)acrylate ester group formed with the free hydroxyls of dextran.

Preferably, the dextran is grafted with methacrylate groups.

The dextran grafted with (meth)acrylate groups can be obtained by reaction of the dextran with (meth)acrylic anhydride. The reaction is advantageously carried out in an aprotic polar solvent medium (for example dimethylformamide, N-methylpyrrolidone, N-ethylpyrrolidone), in particular in the presence of a non-nucleophilic organic or inorganic base, for instance tertiary amines (such as triethanolamine). Preferably, the reaction is carried out at a temperature ranging from 20 to 100° C., in particular for a period of time ranging from 1 to 12 hours

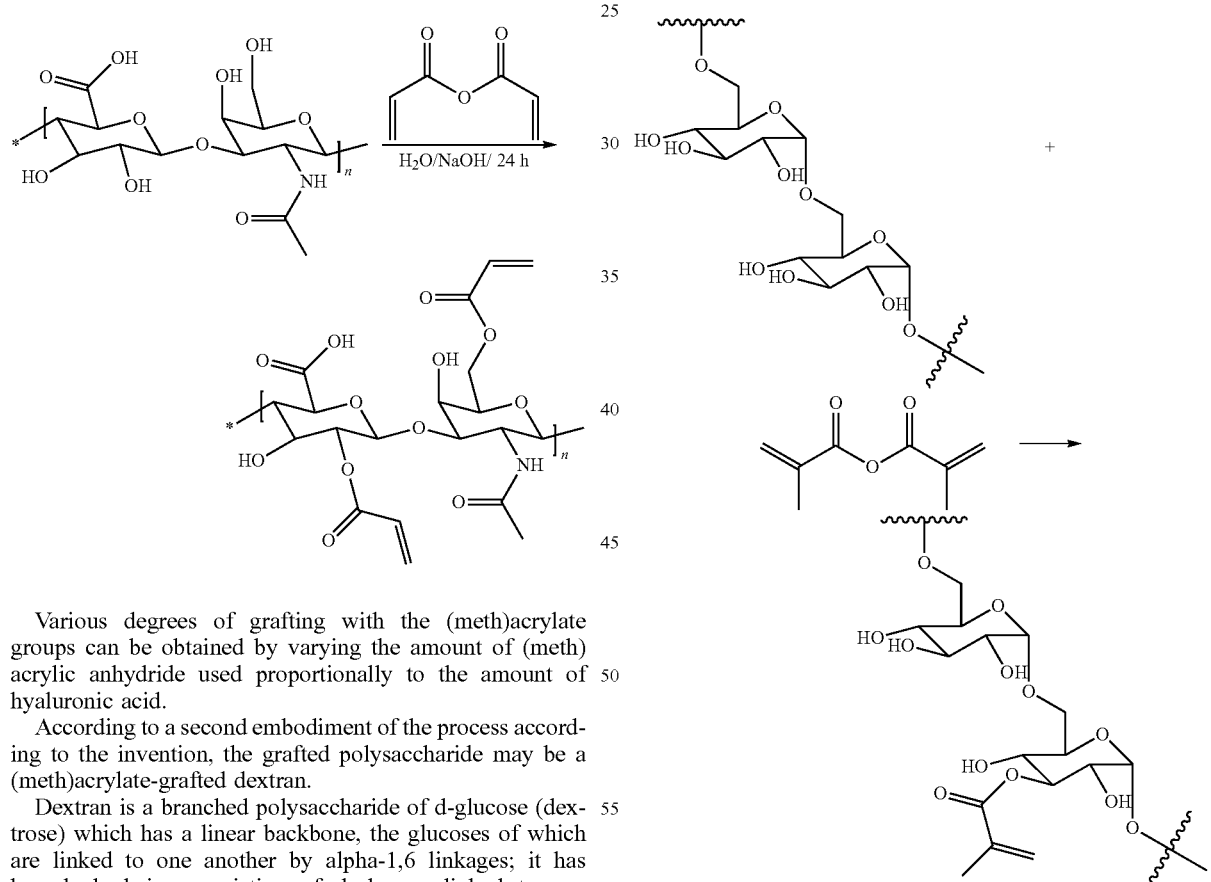

Various degrees of grafting with the (meth)acrylate groups can be obtained by varying the amount of (meth)acrylic anhydride used proportionally to the amount of hyaluronic acid.

According to a second embodiment of the process according to the invention, the grafted polysaccharide may be a (meth)acrylate-grafted dextran.

Dextran is a branched polysaccharide of d-glucose (dextrose) which has a linear backbone, the glucoses of which are linked to one another by alpha-1,6 linkages; it has branched chains consisting of d-glucose linked to one another by alpha-1,2 or -1,3 or -1,4 linkages.

Preferably, the grafted dextran polymer has a weight-average molecular weight ranging from 10 000 to 1 000 000 daltons, more preferentially ranging from 10 000 to 500 000 daltons, and even more preferentially ranging from 15 000 to 350 000 daltons.

The weight-average molecular weight can in particular be determined by liquid chromatography by gel permeation or by size exclusion chromatography.

Various degrees of grafting with the (meth)acrylic groups can be obtained by varying the amount of (meth)acrylic anhydride used proportionally to the amount of dextran, and also the reaction conditions, such as the reaction temperature and time.

According to a third embodiment of the process according to the invention, the grafted polysaccharide may be a (meth)acrylate-grafted carrageenan.

Carrageenans are sulfated polysaccharides which constitute the cell walls of various red algae, from which they can be obtained. Among these red algae, mention may be made, in a non-limiting manner, of *Kappaphycus alvarezii, Eucheuma denticulatum, Eucheuma spinosum, Chondrus crispus, Betaphycus gelatinum, Gigartina skottsbergii, Gigartina canaliculata, Sarcothalia crispata, Mazzaella laminaroides, Hypnea musciformis, Mastocarpus stellatus* and *Iridaea cordata*.

They comprise long galactan chains, made up of disaccharide units. These polysaccharides are composed of alternating (1→3) β-D-galactopyranose (G unit) and (1→4) α-galactopyranose (D unit) or 3,6-anhydro-α-galactopyranose (AnGal unit). Each sugar unit can be sulfated one or more times in position 2, 3, 4 or 6. Methyl and pyruvic acid groups and also other sugar units grafted onto the base structures previously described can also be found. The carrageenans were initially subdivided into subfamilies according to their solubility in KCl, then according to the number and position of the sulfate groups and the presence of 3',6'-anhydro bridges on the galactopyranosyl residues. There are at least about 15 carrageenans listed, the structure of which depends on the alga of origin and the extraction method. Among the most common, mention may be made of the carrageenans below:

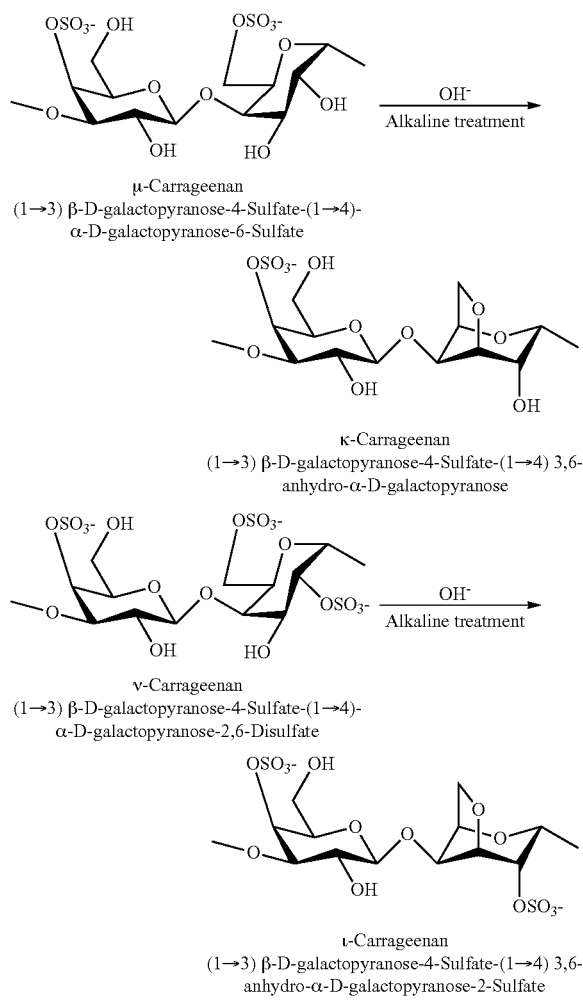

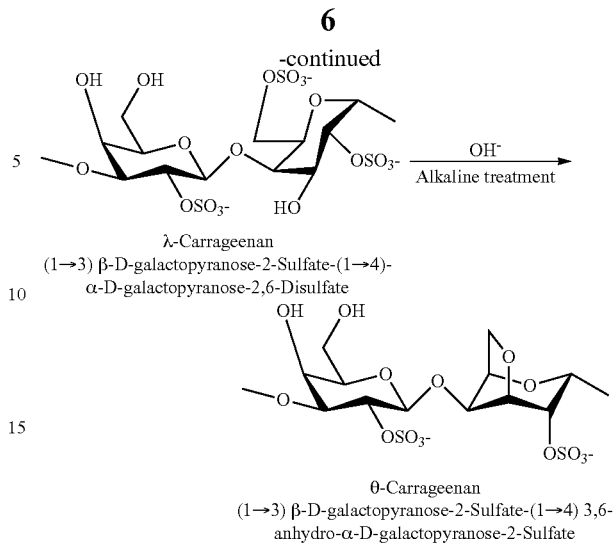

These carrageenans are thus often obtained in the form of mixtures of different structures such as, and in a non-limiting manner, mixtures of κβ, κι, κμ forms.

The carrageenans that can be used may in particular be chosen from carrageenans of μ, κ, ν, ι, λ and θ type. Carrageenans that are particularly suitable for implementing the invention are carrageenans of μ, ν and λ type. Lambda carrageenan is preferably used.

The carrageenans of the present invention can be used in acid form or in salified form. By way of acceptable salts, mention may be made, in a non-limiting manner, of lithium, sodium, potassium, calcium, zinc or ammonium salts.

Preferably, the grafted carrageenan polymer has a weight-average molecular weight ranging from 10 000 to 1 000 000 daltons, more preferentially ranging from 10 000 to 500 000 daltons, and even more preferentially ranging from 15 000 to 350 000 daltons.

The molecular weight can be determined in particular by liquid chromatography, the eluent being 0.1 M sodium chloride and 330 mg/l of sodium azide in water, with dextran as standard, and Wyatt Optilab T-Rex refractometer and Wyatt Dawn-Heleos II light scattering detectors.

Advantageously, the grafted carrageenan polymer has a degree of grafting with (meth)acrylate groups ranging from 2% to 60%, preferably ranging from 2% to 50%, and preferentially ranging from 5% to 30%. The degree of grafting corresponds to the mole percentage of hydroxyl groups of the carrageenan which are grafted with a (meth)acrylate group.

By way of example, a degree of grafting of 50% corresponds to 1.5 acrylate groups grafted onto the 3 hydroxyls of the repeating unit of the carrageenan.

The grafting of the carrageenan with (meth)acrylate groups results from the presence of a (meth)acrylate ester group formed with the free hydroxyls of the carrageenan.

Preferably, the carrageenan is grafted with acrylate groups.

The carrageenan grafted with (meth)acrylate groups can be obtained by reaction of the carrageenan with (meth)acrylic anhydride. The reaction is advantageously carried out in a basic aqueous medium, in particular in the presence of an organic or inorganic base such as, for example, sodium hydroxide. Preferably, the reaction is carried out at a temperature ranging from 5 to 10° C., in particular for a period of time ranging from 24 hours to 48 hours.

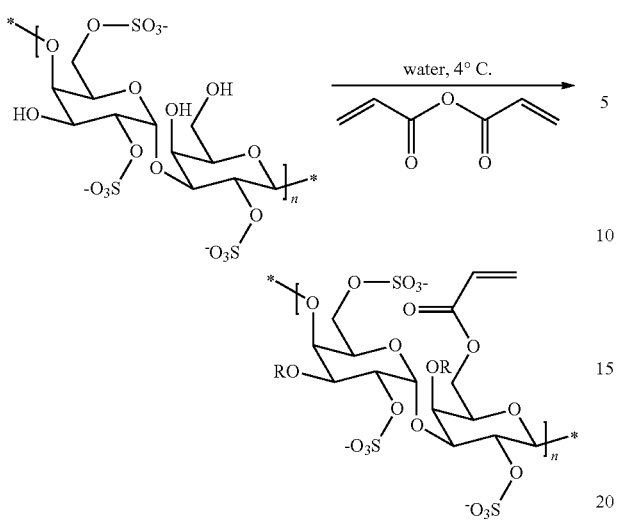

R = H or COCH = CH₂

Various degrees of grafting with the (meth)acrylate groups can be obtained by varying the amount of (meth) acrylic anhydride used proportionally to the amount of carrageenan.

Advantageously, a carrageenan chosen from μ-carrageenan, λ-carrageenan, ν-carrageenans, and preferably λ-carrageenan, is used.

The grafted polysaccharide polymer as previously defined may be present in the composition used according to the invention in a content ranging from 0.1% to 10% by weight, relative to the total weight of the composition, preferably from 0.5% to 10% by weight of active material, preferentially ranging from 1% to 8% by weight, and more preferentially ranging from 1% to 6% by weight.

Advantageously, the grafted polysaccharide is chosen from acrylate-grafted hyaluronic acid, (meth)acrylate-grafted dextran and acrylate-grafted carrageenan.

The second ingredient ii) used in the process of the invention is a photoactive compound.

The term "photoactive compound" [also known as PAC or photoinitiator (PI)] is intended to mean a compound capable of absorbing light and of being converted while generating atoms or molecules comprising a free-radical chemical reactivity (see, for example, *Macromol. Rapid Commun.* Christian Decker, 23, 1067-1093 (2002); *Encyclopedia of Polymer Science and Technology*, "photopolymerisation free radical" http://onlinelibrary.wiley.com/doi/10.1002/0471440264.pst490/pdf; ibid, "photopolymerisation, cationic "ibid, "photopolymerisation, cationic", http://onlinelibrary.wiley.com/doi/10.1002/0471440264.pst491/pdf; *Macromol. Symp.* 143, 45-63 (1999)).

These photoactive compounds are not chemical oxidizing agents such as peroxides, including hydrogen peroxide or hydrogen peroxide-generating systems.

Two major families may be distinguished:
the type I family, in which the photoactive compounds will bring about, under irradiation, a unimolecular cleavage of the covalent bond so as to lead to a free-radical compound also symbolized by a "dot", and
the type II family, in which the photoactive compounds, under irradiation, will lead to a bimolecular reaction in which the excited state of the photoactive compounds interacts with a second molecule (or co-initiator) to generate free radicals.

More particularly, the active compound is chosen from the compounds of formula (I), (II), (III) or (IV), and also organic or inorganic acid salts thereof, optical or geometrical isomers or tautomers thereof, and solvates thereof such as the hydrates:

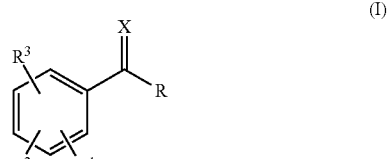

(I)

(II)

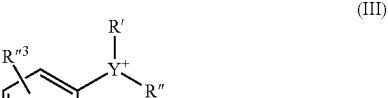

(III)

(IV)

in which formula (I), (II), (III) or (IV):
R represents a group chosen from:
i) $(C_1-C_{10})$alkyl, which is optionally substituted, preferably with one or more atoms or groups chosen from halogen, hydroxyl, $(C_1-C_{10})$alkoxy, (hetero)cycloalkyl comprising between 5 and 10 ring members, such as morpholinyl, and amino $R_aR_bN$— with $R_a$, $R_b$, which may be identical or different, representing a hydrogen atom or a $(C_1-C_{10})$alkyl group or else $R_a$ and $R_b$ form, together with the nitrogen atom which bears them, a heterocycloalkyl group such as morpholino;
ii) $(C_1-C_{10})$alkoxy, which is optionally substituted, preferably with the same substituents as for i) $(C_1-C_{10})$alkyl;
iii) hydroxl;
iv) optionally substituted (hetero)aryl such as optionally substituted phenyl of formula (V)

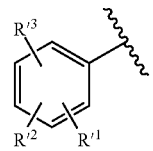

with $R'^1$, $R'^2$, $R'^3$, which may be identical or different, being as defined for $R^1$, $R^2$, $R^3$ and /\/\/\ representing the point of attachment to the rest of the molecule;
v) (hetero)cycloalkyl which is optionally substituted, preferably with a hydroxyl group;
vi) $R^4$—$(X)_n$—$C(X)$—$(X)_n$— with $R^4$ representing an optionally substituted $(C_1-C_{10})$alkyl group, an optionally substituted (hetero)aryl group such as optionally substituted phenyl of formula (V), or an optionally substituted (hetero)cycloalkyl group, n and n', which may be identical or different, being 0 or 1;

vii) $R_cR_dP(X)$— with $R_c$ representing an optionally substituted $(C_1$-$C_{10})$alkyl group or an optionally substituted (hetero)aryl group, and $R_d$ representing an optionally substituted (hetero)aryl group;

viii) or else $R^1$ with R in the ortho position with respect to the C(X)—R group or R" and R"1 in the ortho position with respect to the R'—Y+—R"1 in the ortho position with respect to the R'—Y+—R"+—R" group form, together with the atoms which bear them, a (hetero)cycle fused to the phenyl or (hetero)aryl fused to the phenyl which is optionally substituted in particular on the non-aromatic part with one or more oxo or thiooxo groups; preferably $R^1$ with R in the ortho position with respect to the C(X)—R group form, together with the atoms which bear them and the fused phenyl ring, an anthraquinone group (VI):

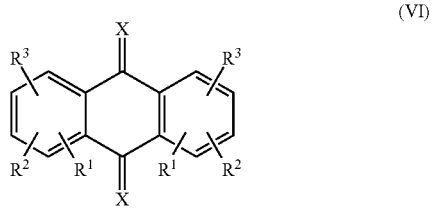

$R^1$, $R^2$ or $R^3$, which may be identical or different, represent i) a hydrogen atom, ii) a halogen atom such as chlorine, iii) an optionally substituted $(C_1$-$C_{10})$alkyl group, iv) $(C_1$-$C_{10})$alkoxy which is optionally substituted in particular with a hydroxyl group, v) optionally substituted (hetero)aryl, vi) optionally substituted (hetero)cycloalkyl, vii) carboxy, viii) cyano, ix) nitro, x) nitroso, xi) —S(O)$_p$—OM with p equalling 1 or 2, M representing a hydrogen atom, an alkali metal or an alkaline-earth metal, xii) $R^4R^5N$—; xiii) $R^4$—$(X)_n$—C(X)—$(X)_{n'}$— with R4, n and n'— with $R^4$, n and n' as previously defined, $R^5$ is as defined for $R^4$ or else $R^4$ and $R^5$ form, together with the nitrogen atom which bears them, an optionally substituted heterocycloalkyl or heteroaryl, such as morpholino, which may be identical or different, equalling 0 or 1, xiv) hydroxyl, or xv) thiol;

R"$^1$, R"$^2$ or R"$^3$, which may be identical or different, are as defined for $R^1$, $R^2$, $R^3$, preferably are chosen from a hydrogen atom or $R^4$—Y— with $R^4$ being as previously defined and preferably a phenyl group;

or else R and $R^1$, which are contiguous, form, together with the carbon atoms which bear them, an optionally unsaturated and optionally substituted (hetero)cycloalkyl group, preferably optionally substituted cycloalkyl, in particular optionally substituted with one or more oxo groups and/or optionally fused with an aryl group such as benzo;

or else two contiguous substituents $R^1$, $R^2$ and/or R'$^1$, R'$^2$ together form a maleic anhydride-derived group such as —C(X)—X—C(X)—;

X, which may be identical or different, represents an oxygen or sulfur atom or an $NR^5$ group with $R^5$ as previously defined, preferably representing a hydrogen atom or a $(C_1$-$C_{10})$alkyl group; more particularly, X represents an oxygen atom;

Y is as defined for X, preferably Y represents a sulfur atom;

Metal represents a transition metal such as iron or chromium, preferably Fe, it being possible for said metal to be cationic, in which case the photoactive compound of formula (VII) comprises a number of anionic counterions An$^-$ as defined hereinafter, making it possible to achieve electro-neutrality of the molecule;

L and L', which may be identical or different, represent a transition metal ligand preferably chosen from the following electron donors C(X) with X as previously defined, cyano CN, $(C_1$-$C_6)$alkenyl, optionally substituted (hetero)aryl, such as bipyridinyl, amines such as the amines $R^4R^5R^6N$ with $R^4$ and $R^5$ as previously defined and $R^6$ representing a hydrogen atom, or a group as defined for $R^4$, phosphine $R^4R^5R^6P$ such as tri(hetero)arylphosphine, (hetero)cycloalkyl which is preferably unsaturated such as cyclopentadiene, carbene such as arduengo carbenes;

q represents an integer inclusively between 1 and 6, making it possible to achieve stability of the metal complex, i.e. so as to obtain an electron number around the Metal equal to 16 or 18 electrons (reference is also made to a 16- or 18-electron coordination sphere);

R' and R", which may be identical or different, represent an optionally substituted (hetero)aryl group;

An$^-$ represents an anionic counterion derived from a salt of an organic or inorganic acid or a halide; more particularly, the anionic counterion is chosen from i) halides such as chloride or bromide; ii) nitrates ; iii) sulfonates, among which the $C_1$-$C_6$ alkylsulfonates: Alk-S(O)$_2$O$^-$ such as methanesulfonate or mesylate and ethanesulfonate; iv) arylsulfonates: Ar—S(O)$_2$O$^{31}$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O$^-$)$_2$—OH O=P(O$^-$)$_3$, HO—[P(O)(O$^-$)]$_w$—P(O)(O$^-$)$_2$ with w being an integer; xiv) acetate; xv) triflate; and xvi) borates such as tetrafluoroborate, xvii) disulfate (O=)$_2$S(O$^-$)$_2$ or SO$_4^{2-}$ and monosulfate HSO$_4^-$. Preferentially, An$^-$ is chosen from (Hal)$_6$P$^-$, or (Hal)$_6$Sb$^-$, with Hal, which may be identical or different, representing a halogen atom such as fluorine; and $R^a$, $R^b$, $R^c$ or $R^d$, which may be identical or different, represent a hydrogen atom or a $(C_1$-$C_{10})$alkyl group.

For the purposes of the present invention and unless otherwise indicated:

an "aryl" radical represents a monocyclic or fused or non-fused polycyclic carbon-based group containing from 6 to 22 carbon atoms, at least one ring of which is aromatic; preferentially, the aryl radical is a phenyl, biphenyl, naphthyl, indenyl, anthracenyl or tetrahydronaphthyl;

a "heteroaryl radical" represents an optionally cationic, 5- to 22-membered, monocyclic or fused or non-fused polycyclic group, comprising from 1 to 6 heteroatoms chosen from nitrogen, oxygen, sulfur and selenium, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and the ammonium salt thereof;

a "cyclic radical" is a non-aromatic, monocyclic or polycyclic, fused or non-fused cycloalkyl radical, containing from 5 to 22 carbon atoms, which may comprise one or more unsaturations;

a "heterocyclic radical" heterocyclic radical" which may contain one or two unsaturations, is a fused or non-fused, 5- to 22-membered monocyclic or polycyclic non-aromatic radical which may contain one or two unsaturations, comprising from 1 to 6 heteroatoms chosen from nitrogen, oxygen, sulfur and selenium;

a "heterocycloalkyl radical" is a saturated heterocyclic radical;

the term "optionally substituted" applied to the alkyl or alkenyl radical implies that said alkyl or alkenyl radical may be substituted with one or more radicals chosen from the following radicals:

i) hydroxyl, ii) C1-C4 alkoxy, iii) acylamino, iv) amino optionally substituted with one or two identical or different C1-C4 alkyl radicals, said alkyl radicals possibly forming with the nitrogen atom that bears them a 5- to 7-membered heterocycle optionally comprising another nitrogen or non-nitrogen heteroatom; v) or a quaternary ammonium group —N+R'R"R'", M- for which R', R" and R'", which may be identical or different, represent a hydrogen atom or a C1-C4 alkyl group, or alternatively —N+R'R"R'"$_1$—C$_4$ alkoxy, iii) acylamino, iv) amino optionally substituted with one or two identical or different C$_1$-C$_4$ alkyl radicals, said alkyl radicals possibly forming with the nitrogen atom that bears them a 5- to 7-membered heterocycle optionally comprising another nitrogen or non-nitrogen heteroatom; v) or a quaternary ammonium group —N$^+$R'R"R'", M- for which R', R" and R'" which may be identical or different, represent a hydrogen atom or a C1-C4 alkyl group, or alternatively —N+R'R"R'"$^-$ for which R', R" and R'", which may be identical or different, represent a hydrogen atom or a C$_1$-C$_4$ alkyl group, or alternatively —N$^+$R'R"R'41 forms a heteroaryl such as imidazolium optionally substituted with a C$_1$-C$_4$ alkyl group, and M$^-$ represents the counterion of the organic or inorganic acid or of the corresponding halide.

According to one preferred mode of the invention, the photoactive compound(s) is (are) chosen from the following compounds:

| Designation | CAS No. | Formula No. |
|---|---|---|
| Benzophenone | 0000119-61-9 | I |
| Benzophenone, 2-methyl- | 0000131-58-8 | I |
| Benzophenone, 4-methyl- | 0000134-84-9 | I |
| Benzoic acid, 2-benzoyl-, methyl ester | 0000606-28-0 | I |
| Benzophenone, 3-methyl- | 0000643-65-2 | I |
| 2-Isopropyl thioxanthone | 0005495-84-1 | I |
| Benzoic acid, 4-(dimethylamino)-, ethyl ester | 0010287-53-3 | I |
| Benzoic acid, p-(dimethylamino)-, 2-ethylhexyl ester | 0021245-02-3 | I |
| Poly(ethylene glycol) bis(p-dimethylaminobenzoate) | 0071512-90-8 | I |
| Phosphine oxide, diphenyl(2,4,6-trimethylbenzoyl)- | 0075980-60-8 | I |
| 4-Isopropyl thioxanthone | 0083846-86-0 | I |
| 1-[4-(2-Hydroxyethoxy)phenyl]-2-hydroxy-2-methyl-1-propane-1-one | 0106797-53-9 | I |
| 1-Butanone, 2-(dimethylamino)-1-[4-(4-morpholinyl)phenyl]-2-(phenylmethyl)- | 0119313-12-1 | I |
| 1-Butanone, 2-(dimethylamino)-2-[(4-methylphenyl)methyl]-1-[4-(4-morpholinyl)phenyl]- | 0119344-86-4 | I |
| Phenyl bis(2,4,6-trimethylbenzoyl) phosphine oxide | 0162881-26-7 | I |
| Benzene, (1-methylethenyl)-, homopolymer, ar-(2-hydroxy-2-methyl-1-oxopropyl) derivs. | 0163702-01-0 | I |
| Oxy-phenyl-acetic acid 2-[2-oxo-2-phenyl-acetoxy-ethoxy]-ethyl ester | 0211510-16-6 | I |
| Oxy-phenyl-acetic 2-[2-hydroxy-ethoxy]-ethyl ester | 0442536-99-4 | I |
| Poly[oxy(methyl-12-ethandiyl)],alpha-[4-(dimethylamino)benzoyl-omega-butoxy | 0223463-45-4 | I |
| 1-(4-[(4-Benzoylphenyl)thio]phenyl)-2-methyl-2-[(4-methylphenyl)sulfonyl]-1-propan-1-one | 0272460-97-6 | I |
| 2-Hydroxy-1-(4-(4-(2-hydroxy-2-methylpropionyl)benzyl)phenyl-2-methyl-2-propanone | 0474510-57-1 | I |
| Di-ester of carboxymethoxy benzophenone and polytetramethyleneglycol 250 | 0515136-48-8 | I |
| Di-ester of carboxymethoxy-benzophenone and polyethylene glycol 200 | 0515136-49-9 | I |
| Poly(oxy-1,4-butanediyl), .alpha.-[2-[(9-oxo-9H-thioxanthenyl)oxy]acetyl]-.omega.-[[2-[(9-oxo-9H-thioxanthenyl)oxy]acetyl]oxy]- | 0813452-37-8 | I |
| 4-(2-hydroxyethoxy)phenyl-(2-hydroxy-2-propyl)cétone | 0106797-53-9 | I |
| (Methylamino)diethane-2,1-diylbis(4-dimethylamino amino benzoate) | | |
| Anthraquinone, 2-ethyl- | 0000084-51-5 | I |
| Thioxanthen-9-one, 2-chloro- | 0000086-39-5 | I |
| Benzophenone, 4,4'-bis(diethylamino)- | 0000090-93-7 | I |
| Phosphine oxide, triphenyl- | 0000791-28-6 | I |
| Methanone, (1-hydroxycyclohexyl)phenyl- | 0000947-19-3 | I |
| Methanone, phenyl(2,4,6-trimethylphenyl)- | 0000954-16-5 | I |
| Glyoxylic acid, phenyl-, ethyl ester | 0001603-79-8 | I |
| 4-Phenylbenzophenone | 0002128-93-0 | I |
| Benzoic acid, 2-(dimethylamino)ethyl ester | 0002208-05-1 | I |
| Acetophenone, 2,2-diethoxy- | 0006175-45-7 | I |
| 1-Propanone, 2-hydroxy-2-methyl-1-phenyl- | 0007473-98-5 | I |
| 1,2-Propanedione, 1-phenyl-, 2-[O-(ethoxycarbonyl)oxime] | 0065894-76-0 | I |
| Benzoic acid, 4-(dimethylamino)-, 2-butoxyethyl ester | 0067362-76-9 | I |
| 1-Propanone, 1-[4-(1,1-dimethylethyl)phenyl]-2-hydroxy-2-methyl- | 0068400-54-4 | I |
| 1-Propanone, 2-methyl-1-[(4-methylthio)phenyl]-2-(4-morpholinyl)- | 0071868-10-5 | I |
| Glyoxylic acid, phenyl-, methyl ester | 0015206-55-0 | I |
| 2,2-Dimethoxy-2-phenylacetophenone | 0024650-42-8 | I |
| Methyl-2-benzoylbenzoate | 0000606-28-0 | I |
| 2-Benzyl-2-(dimethylamino)-4-morpholino butyrophenone | 0119313-12-1 | I |
| Ethyl-4-Dimethylaminobenzoate | 0010287-53-3 | I |
| 2,4-Diethyl-9H-thioxanthen-9-on | 0082799-44-8 | I |
| 9H-Thioxanthene-2-carboxylic acid, 9-oxo-, ethyl ester | 0083817-60-1 | I |
| Methanone, [4-[(4-methylphenyl)thio]phenyl]phenyl- | 0083846-85-9 | I |
| Phosphinic acid, phenyl(2,4,6-trimethylbenzoyl)-, ethyl ester | 0084434-11-7 | I |
| 1-Chloro-4-propoxythioxanthone | 0142770-42-1 | I |
| Phosphine oxide, bis(2,6-dimethoxybenzoyl) (2,4,4-trimethylpentyl)-(9Cl) | 0145052-34-2 | I |
| 4,4'-Bis(methylethylamino)benzophenone | 0194655-98-6 | I |
| Oxirane, 2-methyl-, polymer with oxirane, 2-benzoylbenzoate | 1003557-16-1 | I |

| Designation | CAS No. | Formula No. |
|---|---|---|
| {a-4-(Dimethylamino)benzoylpoly (oxyethylene)-poly[oxy(1-methylethylene)]- poly(oxyethylene)} 4-(dimethylamino)benzoate | 1003557-17-2 | I |
| 1,3-Di({a-2-(phenylcarbonyl)benzoylpoly [oxy(1-methylethylene)]}oxy)-2,2-bis({a-2-(phenylcarbonyl) benzoylpoly[oxy(1-methylethylene)]} oxymethyl)propane | 1003567-82-5 | I |
| 1,3-Di({a-[1-chloro-9-oxo-9H-thioxanthen-4-yl)oxy]acetylpoly[oxy(1-methylethylene)]} oxy)-2,2-bis({a-[1-chloro-9-oxo-9H-thioxanthen-4-yl)oxy]acetylpoly[oxy(1-methylethylene)]}oxymethyl)propane | 1003567-83-6 | I |
| 1,3-Di({-4-(dimethylamino)benzoylpoly [oxy(1-methylethylene)]}oxy)-2,2-bis({-4-(dimethylamino)benzoylpoly[oxy(1-methylethylene)]}oxymethyl) propane | 1003567-84-7 | I |
| Poly(oxy-1,2-ethanediyl), a-[2-(4-chlorobenzoyl)benzoyl]-w-[[2-(4-chlorobenzoyl)benzoyl]oxy]- | 1007306-69-5 | I |
| 2-Propenoic acid, 1,1'-[9-[[(1-fluoro-9-oxo-9H-thioxanthen-4-yl)oxy]methyl]-7,12-dimethyl-3,6,8,11,13,16-hexaoxaoctadecane-1,18-diyl] ester | 1253390-33-8 | I |
| 2,3-Dihydroxy-6-(2-hydroxy-2-methyl-1-oxopropyl)-1,1,3-trimethyl-3-[4-(2-hydroxy-2-methyl-1-oxopropyl)phenyl]-1H-indene | | I |
| 2-Hydroxy-[4'-(2-Hydroxypropoxy) phenyl]-2-methylpropanone | | I |
| Polyethylene glycol (200) di(β-4[p-acetylphenyl]piperazine) propionate | | I |
| Polyethylene glycol (200) di-β-4[4-(2-dimethylamino-2-benzyl)butanoylphenyl]piperazine) propionate | | I |
| 2-Hydroxy-4'-(2-hydroxyethoxy)-2-methylpropiophenone | | I |
| 1,3-Di({a-2-(phenylcarbonyl)benzoylpoly [oxy(1-methylethylene)]}oxy)-2,2-bis({a-2-(phenylcarbonyl) benzoylpoly[oxy(1-methylethylene)]} oxymethyl)propane | 1003567-82-5 | I |
| 1,3-Di({a-2-(phenylcarbonyl)benzoylpoly [oxy(1-methylethylene)]}oxy)-2,2-bis({a-2-(phenylcarbonyl) benzoylpoly[oxy(1-methylethylene)]} oxymethyl)propane | 1003567-82-5 | I |
| 1,3-Di({-4-(dimethylamino)benzoylpoly[oxy (1-methylethylene)]}oxy)-2,2-bis({-4-(dimethylamino)benzoylpoly[oxy(1-methylethylene)]}oxymethyl) propane | 1003567-84-7 | I |
| Bis (eta(5)-cyclopentadienyl)-bis(2,6-difluoro-3-[pyrrol-1-yl]-phenyl)titanium | 0125051-32-3 | II |
| Iodonium, bis(4-methylphenyl)-, hexafluorophosphate(1-) | 0060565-88-0 | III |
| Bis(4-tert-butylphenyl) iodonium hexafluorophosphate | 0061358-25-6 | III |
| Sulfonium, diphenyl[(phenylthio)phenyl]-, hexafluorophosphate(1-) (1:1) | 0068156-13-8 | III |
| Sulfonium, diphenyl[4-(phenylthio)phenyl]-, (OC-6-11)-hexafluoroantimonate(1-) (1:1) | 0071449-78-0 | III |
| Iodonium, bis(4-dodecylphenyl)-, (OC-6-11)-hexafluoroantimonate(1-) (1:1) | 0071786-70-4 | III |
| Bis(4-diphenylsulfonium)phenylsulfide-bis (hexafluorophosphate) | 0074227-35-3 | III |
| Diphenyl[(phenylthio)phenyl]sulfonium hexafluorophosphate | 0075482-18-7 | III |
| Triphenyl sulfonium hexafluorophosphate (mono + di)salts | 0086481-78-9 | III |
| Thiobis(4,1-phenylene)-S,S,S',S'-tetraphenyldisulfonium bishexafluoroantimonate | 0089452-37-9 | III |
| Triphenylsulfonium hexafluorophosphate | 0104558-95-4 | III |
| Iodonium, [4-(1-methylethyl)phenyl](4-methylphenyl)-, tetrakis(2,3,4,5,6-pentafluorophenyl)borate(1-) (1:1) | 0178233-72-2 | III |
| Iodonium, (4-methylphenyl)[4-(2-methylpropyl)phenyl]-, hexafluorophosphate(1-) | 0344562-80-7 | III |
| 9H-Thioxanthenium, 10-[1,1'biphenyl]-4-yl-2-(1-methylethyl)-9-oxo, hexafluorophosphate | 0591773-92-1 | III |
| d,l-Camphorquinone | 0010373-78-1 | IV |

Use may also be made, as photoactive compounds, of:

| Designation | CAS No. | Formula No. |
|---|---|---|
| 1H-Imidazole, 2-(2-chlorophenyl)-1-[2-(2-chlorophenyl)-4,5-diphenyl-2H-imidazol-2-yl]-4,5-diphenyl- | 0007189-82-4 | — |
| Anthracene, 9,10-dibutoxy | 0076275-14-4 | — |
| Phenoxyethylacrylate | 0048145-04-6 | — |
| Tryptophan | 000073-22-3 | — |

As photoactive compound, mention may also be made of the dyes referred to as "photosensitizing dyes", such as ethyl eosin, eosin Y, fluorescein, rose bengal, methylene blue, erythrosine, phloxime, thionine, riboflavin and methylene green.

According to one particular embodiment of the invention, use will be made of a combination of photoactive compounds containing 1 to 5 photoactive compounds as a mixture in particular in proportions of 0.001% to 4% by weight for each photoactive compound, relative to the total weight of the composition.

The particularly preferred photoactive compounds are chosen from:

| Designation | CAS No. | Formula No. |
|---|---|---|
| Poly(ethylene glycol) bis(p-dimethylaminobenzoate) | 0071512-90-8 | I |
| 1-[4-(2-Hydroxyethoxy)phenyl]-2-hydroxy-2-methyl-1-propane-1-one | 0106797-53-9 | I |
| 1-Butanone, 2-(dimethylamino)-1-[4-(4-morpholinyl)phenyl]-2-(phenylmethyl)- | 0119313-12-1 | I |
| Phenyl bis(2,4,6-trimethylbenzoyl) phosphine oxide | 0162881-26-7 | I |
| Benzene, (1-methylethenyl)-, homopolymer, ar-(2-hydroxy-2-methyl-1-oxopropyl) derivs. | 0163702-01-0 | I |
| 2-Hydroxy-4'-(2-hydroxyethoxy)-2-methylpropiophenone | 0106797-53-9 | I |
| Oxy-phenyl-acetic acid 2-[2-oxo-2-phenyl-acetoxy-ethoxy]-ethyl ester | 0211510-16-6 | I |
| Oxy-phenyl-acetic 2-[2-hydroxy-ethoxy]-ethyl ester | 0442536-99-4 | I |
| Poly[oxy(methyl-12-ethandiyl)], alpha-[4-(di-methylamino)benzoyl-omega-butoxy | 0223463-45-4 | I |
| 2-Hydroxy-1-(4-(4-(2-hydroxy-2-methylpropionyl)benzyl)phenyl-2-methyl-2-propanone | 0474510-57-1 | I |
| 4-(2-hydroxyethoxy)phenyl-(2-hydroxy-2-propyl)ketone | 0106797-53-9 | I |
| d,l-Camphorquinone | 0010373-78-1 | IV |
| 2,2-Dimethoxy-2-phenylacetophenone | 0024650-42-8 | I |
| 1-Propanone, 1-[4-(1,1-dimethylethyl) phenyl]-2-hydroxy-2-methyl- | 0068400-54-4 | I |
| 1-Propanone, 2-methyl-1-[(4-methylthio)phenyl]-2-(4-morpholinyl)- | 0071868-10-5 | I |
| 4,4'-Bis(methylethylamino)benzophenone | 0194655-98-6 | I |
| {a-4-(Dimethylamino)benzoylpoly (oxyethylene)-poly[oxy(1-methylethylene)]-poly(oxyethylene)}4-(dimethylamino) benzoate | 1003557-17-2 | I |
| 1,3-Di({a-2-(phenylcarbonyl)benzoylpoly[oxy(1-methylethylene)]}oxy)-2,2-bis({a-2-(phenylcarbonyl) benzoylpoly[oxy(1-methylethylene)]} oxymethyl)propane | 1003567-82-5 | I |

-continued

| Designation | CAS No. | Formula No. |
|---|---|---|
| 1,3-Di({-4-(dimethylamino)benzoylpoly[oxy(1-methylethylene)]}oxy)-2,2-bis({-4-(dimethylamino)benzoylpoly[oxy(1-methylethylene)]}oxymethyl) propane | 1003567-84-7 | I |
| Poly(oxy-1,2-ethanediyl), a-[2-(4-chlorobenzoyl)benzoyl]-w-[[2-(4-chlorobenzoyl)benzoyl]oxy]- | 1007306-69-5 | I |
| 2-Hydroxy-[4'-(2-Hydroxypropoxy)phenyl]-2-methylpropanone | | I |
| Polyethylene glycol (200) di(β-4[p-acetylphenyl]piperazine) propionate | | I |
| Polyethylene glycol (200) di(β-4[4-(2-dimethylamino-2-benzyl)butanoylphenyl]piperazine) propionate | | I |

Preferentially, the photoactive compound denotes 2-hydroxy-4'-(2-hydroxyethoxy)-2-methylpropiophenone.

The photoactive compound (or the mixture of photoactive compounds) is preferably present in the composition in an amount ranging from 0.001% to 20% by weight, relative to the total weight of the composition, preferably ranging from 0.01% to 10% by weight, preferentially ranging from 0.05% to 5% by weight, even better still ranging from 0.1% to 3% by weight.

The photoactive compound may advantageously be present in the composition according to the invention according to a photoactive compound/(meth)acrylate-grafted polysaccharide weight ratio ranging from 0.025 to 0.035, preferably ranging from 0.027 to 0.033, and preferentially ranging from 0.029 to 0.031.

The composition used according to the invention is generally suitable for topical application to the skin and thus generally comprises a physiologically acceptable medium, i.e. a medium that is compatible with the skin and/or skin appendages. It is preferably a cosmetically acceptable medium, i.e. a medium which has a pleasant colour, odour and feel and which does not cause any unacceptable discomfort (stinging, tautness or redness) liable to discourage the consumer from using this composition.

The composition according to the invention may be in any galenic form conventionally used for a topical application and especially in the form of dispersions of aqueous gel or lotion type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/W or O/W/O), microemulsions, vesicular dispersions of ionic and/or non-ionic type, or wax/aqueous phase dispersions. These compositions are prepared according to the usual methods.

According to one preferred embodiment of the invention, the composition is in the form of an O/W emulsion or an aqueous gel.

Advantageously, the composition used according to the invention comprises water, in particular in a content which can range from 10% to 99% by weight and preferably ranging from 50% to 99% by weight, relative to the total weight of the composition.

The composition used according to the invention may also contain one or more attachments commonly used in the cosmetics field, such as emulsifiers, preservatives, sequestering agents, fragrances, thickeners, oils, waxes or film-forming polymers.

Needless to say, those skilled in the art will take care to select this or these optional additional compound(s), and/or the amount thereof, such that the anti-wrinkle properties of the composition according to the invention are not, or are not substantially, adversely affected by the envisaged addition.

According to this step of the process, it is possible to apply 0.01 to 0.5 g of cosmetic composition comprising the grafted polysaccharide polymer and the photoactive agent, in particular 0.05 to 0.1 g of composition, per cm$^2$ of skin.

The process according to the invention also comprises a step consisting in exposing the skin to light radiation preferably having a wavelength of between 360 and 600 nm.

It is possible to perform this step consisting in applying light radiation after or at the same time as (simultaneously with) the step consisting in applying to the skin the composition comprising the grafted polysaccharide polymer and the photoactive agent. Preferably, the two steps are carried out simultaneously.

Preferentially, firstly, the composition comprising the grafted polysaccharide polymer and the photoactive agent is applied to the skin, and then, secondly, light radiation is applied to the skin.

It is possible to leave the composition comprising the grafted polysaccharide polymer and the photoactive agent on for a period, before carrying out the step of applying the light radiation.

Preferably, the light radiation used in the process according to the invention has a wavelength of between 400 and 480 nm.

The light radiation preferably has a flux (amount of energy per unit surface area) ranging from 3 to 100 J/cm$^2$ and preferably ranging from 3 to 10 J/cm$^2$.

The light radiation may be continuous or non-continuous light.

The light radiation may be natural light (daylight).

The light radiation may be generated by a device, such as arc lamps such as xenon lamps and mercury lamps; fluorescent lamps; incandescent lamps such as halogens; LEDs and lasers.

Mention may be made especially of goLITE BLU from the company Philips, the lamp Energylight HF 3319/01 from the company Philips, the lamps Dayvia White and Messa from the company Solvital, the lamp Lumino Plus from the company Lanaform, the lamp Medibeam from the company Medibeam, the lamp M-LED 01 from the company Meimed, the lamp Lifemax Light Pod from the company Lifemax, the lamp Lite-Pad from the company Reicorp, and the lamp Camag Box 3 (4×8 W) from the company Camag.

The exposure time of the treated skin to the light radiation provided by a device is preferably at least 5 seconds. Preferably, this exposure time can range from 10 seconds to 15 minutes, in particular between 15 seconds and 10 minutes, even better still between 20 seconds and 5 minutes, regardless of the order of the steps (one before the other or simultaneous).

By way of example, in the case of simultaneous application of the light radiation provided by a device and of the composition comprising the (meth)acrylate-grafted polysaccharide polymer and the photoactive compound, the light-exposure time can advantageously range from 5 seconds to 15 minutes.

By way of example, in the case of application of the composition according to the invention and then exposure to the light radiation provided by a device, the light-exposure time can advantageously be between 5 seconds and 15 minutes. It is possible to leave the composition used according to the invention on for a period of 1 second to 3 hours, before carrying out the step of applying the light radiation. It is possible to carry out rinsing of the composition, after the step of exposure to light radiation.

The exposure time of the treated skin to daylight as light radiation is preferably at least 3 minutes. Preferably, this exposure time can range from 3 minutes to 12 hours, in particular between 5 minutes and 90 minutes, even better still between 10 minutes and 30 minutes, regardless of the order of the steps (one before the other or simultaneous).

By way of example, in the case of simultaneous application of daylight and of the composition comprising the (meth)acrylate-grafted polysaccharide and the photoactive compound, the light-exposure time can advantageously range from 3 minutes to 12 hours. It is possible to carry out rinsing of the composition, after the step of exposure to light radiation.

By way of example, in the case of application of the composition of (meth)acrylate-grafted polysaccharide and the photoactive compound and then exposure to daylight, the light-exposure time can advantageously be between 3 minutes and 12 hours. It is possible to leave the composition according to the invention on for a period of 1 second to 3 hours, before carrying out the step of exposure to light radiation.

It is possible to carry out rinsing of the composition, after the step of exposure to light radiation.

The step of exposure to light radiation can be repeated several times during the day.

The application of the cosmetic composition used according to the invention is carried out according to the usual techniques, for example by application (in particular of creams, gels, sera or lotions) to the skin intended to be treated, in particular facial and/or neck skin, especially the skin of the area around the eyes. In the context of this process, the composition may, for example, be a care composition.

The invention will now be described with reference to the examples that follow, which are given as non-limiting illustrations. The contents are expressed as percentage by weight.

SYNTHESIS EXAMPLE 1 (POLYMER 1)

Dextran 33%-functionalized with Methacrylate Groups 10 g of dextran (sold under the reference 406261000 by the company Acros) were suspended in 40 ml of a lithium chloride/dimethylformamide mixture (at 10% by weight of LiCl) and the suspension was heated to 100° C. 20 ml of the lithium chloride/dimethylformamide mixture were added until complete dissolution of the dextran. The mixture was then cooled to 80° C., then 0.56 g of triethanolamine was added, the mixture was stirred for 15 minutes at 80° C., then 8.55 g of methacrylic anhydride were slowly added (10 minutes). The mixture was left to stir for 5 hours at 70° C. and was then left to return to ambient temperature (25° C.). The reaction mixture was then poured into 150 ml of isopropanol, stirred for 1 hour and then filtered. 11.8 g of a white solid were obtained.

Analyses:
$^1$H NMR D$_2$O:1 OH unit functionalized for 3 OH units available.

The dextran obtained is 33%-functionalized with acrylate groups.

SYNTHESIS EXMPLE 2 (POLYMER 2)

Hyaluronic Acid 60%-functionalized with Acrylic Anhydride

In a thermostated reactor, 5 g of hyaluronic acid (Hyacare® 50 from Evonik) were dissolved in 100 ml of water and the mixture was maintained at a temperature of 7° C., then 14.8 g of acrylic anhydride were added dropwise over the course of approximately 2 min. The pH was adjusted to 7.7 by slowly adding (over the course of approximately one hour) sodium hydroxide at 30% in water (7 M). The mixture was left to react for 24 hours. The mixture obtained was purified by dialysis (polymer in 150 ml of water, 3.3% by weight) on a Spectra/Por® 15 kDa membrane for 5 days in 5 liters of water (water changed 4 times, i.e. 20 liters in total), then the purified fraction was lyophilized by freezing with a mixture of dry ice and acetone at −80° C., and by placing the frozen mixture in a lyophilization apparatus for 4 days.

2.5 g of a white solid were obtained.
Analyses:
$^1$H NMR D$_2$O:2.45 (7.36/3) OH units functionalized for 4 OH units available.

The hyaluronic acid obtained is 60%-functionalized with acrylate groups.

EXAMPLE 1

Demonstration of the Tensioning Effect of the Polymer 1 Used According to the Invention
The following compositions were prepared:
Composition A: aqueous solution of polymer 1 at 5% AM
Composition B: ethanolic solution of 2-hydroxy-4'-(2-hydroxyethoxy)-2-methylpropiophenone at 5% AM (photoactive compound)
Composition C: mixture of 100 µl of composition A and 10 µl of composition B
Composition R: aqueous composition of Hybridur® 875 polymer dispersion from Air Products (aqueous dispersion at 40% by weight of particles of an inter-penetrated network of polyurethane and acrylic polymers) at 7% AM The tensioning capacity of polymer 1 used was compared, in vitro, to a reference tensioning polymer: Hybridur® 875 polymer dispersion from Air Products (aqueous dispersion at 40% by weight of particles of an interpenetrated network of polyurethane and acrylic polymers). The polymer to be evaluated was deposited on a nitrile rubber strip cut from a glove sold under the reference Safeskin Nitrile Criticial No. 038846 by the company Dominique Dutscher S A, having a surface area of 3.5 cm$^2$, stretched taut beforehand on a support. An aqueous solution containing the polymer to be evaluated was therefore deposited on the elastomer strip, by depositing 1.8 mg (of solids) of polymer.

For the tensioning reference, 26 µl of an aqueous solution containing 7% AM of Hybridur® 875 polymer (composition R) were thus deposited on a nitrile rubber strip so as to thus obtain a reference tensioning strip.

26 µl of composition C containing the mixture of polymer 1 and the photoactive compound were deposited on another strip, then the treated strip was irradiated for 15 seconds with a light source: Xenon lamp (reference OMNI300 from the company Lot-Oriel) coupled to a computer and a monochromator with the following characteristics: Wavelength of 430 nm and power of 15 mW/cm$^2$ (power measured at the surface of the strip). Dose of irradiation received at the surface after 15 seconds equals 225 mJ/cm$^2$.

After drying for 24 hours at ambient temperature (25° C.), the tensioning effect obtained was measured by observing the curving (retraction) of the strip treated with polymer 1, in comparison with that obtained with the control (Hybridur® 875).

The persistence of the tensioning effect (i.e. the retaining of the tensioning effect in the face of perspiration or washing) was then evaluated by rinsing the treated nitrile strips with a 0.9 M aqueous NaCl solution (10 ml of the saline solution are projected onto the strip at a distance of 5 cm using a pipette). The strip was left to dry for 3 hours and the tensioning effect (the curving (retraction) of the strip) was again observed, comparing it with the effect obtained before rinsing.

The tensioning effect of polymer 1 alone (composition A) without irradiation was also evaluated.

The following results were obtained:

| Polymer tested | Tensioning effect | Tensioning effect after washing with water |
| --- | --- | --- |
| Hybridure 875 reference (Composition R without irradiation) | correct | correct |
| Example 1 (composition E with irradiation) | greater than the reference | greater than the reference |
| Polymer 1 (composition A without irradiation) | Comparable to the reference | Less than the reference |

The results obtained show that polymer 1 mixed with the photoactive compound (composition E) after irradiation has a good tensioning effect, including after washing with water. The tensioning effect obtained is greater than that of polymer 1 used alone without irradiation.

EXAMPLE 2

Demonstration of the Tensioning Effect of Polymer 2 Used According to the Invention The following composition was prepared:
Composition D: aqueous solution of polymer 2 at 1.67% AM Three mixtures of compositions D and B as described in the table hereinafter were prepared and their tensioning effect was evaluated according to the protocol described in Example 1 (deposition of 26 µl of the composition to be evaluated on the strip).

The following results were obtained:

| Polymer tested | Tensioning effect | Tensioning effect after washing with water |
| --- | --- | --- |
| Hybridure 875 reference (Composition R without irradiation) | correct | correct |
| 100 µl composition D + 40 µl composition B (Example 2a) | comparable to the reference | comparable to the reference |
| 100 µl composition D + 20 µl composition B (Example 2b) | comparable to the reference | comparable to the reference |
| 100 µl composition D + 2 µl composition B (Example 2c) | comparable to the reference | Less than the reference |
| 100 µl composition D (without photoactive compound and without irradiation) (Example 2') | Less than the reference | No tensioning effect |

The results obtained show that the application of the mixtures of polymer 2 and the photoactive compound (Examples 2a, 2b, 2c), after irradiation, makes it possible to obtain a good tensioning effect, including after washing with water.

The tensioning effect obtained with the mixtures is greater than that of polymer 2 used alone without irradiation.

EXAMPLE 3

An anti-wrinkle gel having the following composition is prepared:

| | |
| --- | --- |
| polymer of Example 1 | 1 g |
| hydroxyethylcellulose (Natrosol ® 250 HHR CS from Ashland) | 0.5 g |
| 2-Hydroxy-4'-(2-hydroxyethoxy)-2-methylpropiophenone | 0.05 g |
| Preservatives qs | |
| Water qs | 100 g |

The composition obtained is applied to the face and then the surface of the treated skin is irradiated with white light (Lite-Pad lamp from the company Reicorp) for 30 seconds. The treatment applied makes it possible to effectively smooth out the wrinkles.

EXAMPLE 4

An anti-wrinkle gel having the following composition is prepared:

| | |
| --- | --- |
| polymer of Example 2 | 1 g |
| hydroxyethylcellulose (Natrosol ® 250 HHR CS from Ashland) | 0.5 g |
| 2-Hydroxy-4'-(2-hydroxyethoxy)-2-methylpropiophenone | 0.01 g |
| Preservatives qs | |
| Water qs | 100 g |

The composition obtained is applied to the face and then the surface of the treated skin is irradiated with white light (Lite-Pad lamp from the company Reicorp) for 30 seconds. The treatment applied makes it possible to effectively smooth out the wrinkles.

The invention claimed is:

1. A cosmetic process for caring for the skin comprising:
 (i) applying to the skin a composition comprising, in a physiologically acceptable medium, a polysaccharide polymer grafted with (meth)acrylate groups wherein the grafted polysaccharide is selected from the group consisting of (meth)acrylate-grafted hyaluronic acid, (meth)acrylate-grafted dextran and (meth)acrylate-grafted carrageenan, and a photoactive compound,
 (ii) followed by exposing the skin to light radiation.

2. The process according to claim 1, wherein the grafted polysaccharide polymer has a degree of grafting ranging from 10% to 80%.

3. The process according to claim 1, wherein the grafted polysaccharide polymer is selected from the group consisting of hyaluronic acid grafted with acrylate groups, dextran grafted with methacrylate groups and carrageenan grafted with acrylate groups.

4. The process according to claim 1, wherein the grafted polysaccharide polymer has a weight-average molecular weight ranging from 5000 to 1 000 000 daltons.

5. The process according to claim 1, wherein the grafted polysaccharide polymer is present in the composition in a content ranging from 0.1% to 10% by weight, relative to the total weight of the composition.

6. The process according to claim 1, in which the photoactive compound is selected from the group consisting of the compounds of formula (I), (II), (III) or (IV), organic or inorganic acid salts thereof, optical or geometrical isomers or tautomers thereof, and solvates thereof:

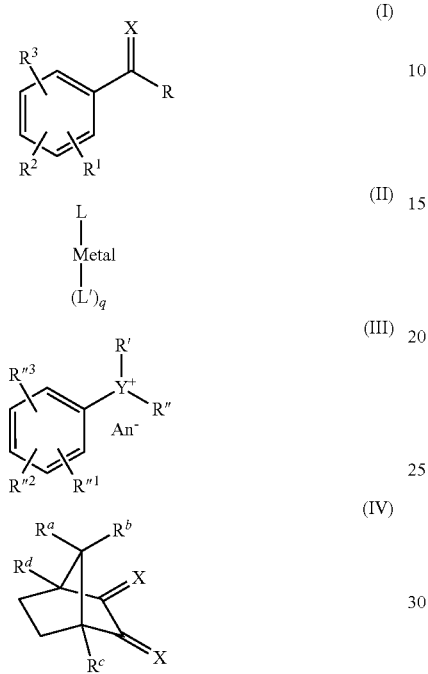

in which formula (I), (II), (III) or (IV):
R represents a group selected from the group consisting of:
i) $(C_1-C_{10})$alkyl, which is optionally substituted,
ii) $(C_1-C_{10})$alkoxy, which is optionally substituted;
iii) hydroxyl;
iv) optionally substituted (hetero)aryl;
v) (hetero)cycloalkyl which is optionally substituted;
vi) $R^4$—$(X)_n$—$C(X)$—$(X)_{n'}$— with $R^4$ representing an optionally substituted $(C_1-C_{10})$alkyl group, an optionally substituted (hetero)aryl group, or an optionally substituted (hetero)cycloalkyl group, n and n', which may be identical or different, being 0 or 1;
vii) $R_cR_dP(X)$— with $R_c$ representing an optionally substituted $(C_1-C_{10})$alkyl group or an optionally substituted (hetero)aryl group, and $R_d$ representing an optionally substituted (hetero)aryl group;
viii) or else $R^1$ with R in the ortho position with respect to the C(X)—R group or R" and R"1 in the ortho position with respect to the R'—Y+—R"¹ in the ortho position with respect to the R'—Y+—R"⁺—R" group form, together with the atoms which bear them, a (hetero)cycle fused to the phenyl or (hetero)aryl fused to the phenyl which is optionally substituted
$R^1$, $R^2$ or $R^3$, which may be identical or different, represent i) a hydrogen atom, ii) a halogen atom, iii) an optionally substituted $(C_1-C_{10})$alkyl group, iv) $(C_1-C_{10})$alkoxy which is optionally substituted, v) optionally substituted (hetero)aryl, vi) optionally substituted (hetero)cycloalkyl, vii) carboxy, viii) cyano, ix) nitro, x) nitroso, xi) —$S(O)_p$—OM with p equalling 1 or 2, M representing a hydrogen atom, an alkali metal or an alkaline-earth metal, xii) $R^4R^5N$—;

xiii) $R^4$—$(X)_n$—$C(X)$—$(X)_{n'}$— with R4, n and n'- with $R^4$, n and n' as previously defined, $R^5$ is as defined for $R^4$ or $R^4$ and $R^5$ form, together with the nitrogen atom which bears them, an optionally substituted heterocycloalkyl or heteroaryl which may be identical or different, equalling 0 or 1, xiv) hydroxyl, or xv) thiol;
$R"^1$, $R"^2$ or $R"^3$, which may be identical or different, are as defined for $R^1$, $R^2$, $R^3$;
or else R and $R^1$, which are contiguous, form, together with the carbon atoms which bear them, an optionally unsaturated and optionally substituted (hetero)cycloalkyl group;
or two contiguous substituents $R^1$, $R^2$ and/or $R'^1$, $R'^2$ together form a maleic anhydride-derived group;
X, which may be identical or different, represents an oxygen or sulfur atom or an $NR^5$ group with $R^5$ as previously defined;
Y is as defined for X;
Metal represents a transition metal which can be cationic, in which case the photoactive compound of formula (VII) comprises an anionic counterion An⁻ as defined hereinafter, making it possible to achieve electro-neutrality of the molecule;
L and L', which may be identical or different, represent a transition metal ligand;
q represents an integer inclusively between 1 and 6, making it possible to achieve stability of the metal complex, so as to obtain an electron number around the Metal equal to 16 or 18 electrons (reference is also made to a 16- or 18-electron coordination sphere);
R' and R", which may be identical or different, represent an optionally substituted (hetero)aryl group;
An⁻ represents an anionic counterion derived from a salt of an organic or inorganic acid or a halide; and
$R^a$, $R^b$, $R^c$ or $R^d$, which may be identical or different, represent a hydrogen atom or a $(C_1-C_{10})$alkyl group.

7. The process according to claim 1, in which the photoactive compound is selected from the group consisting of the following compounds:
Poly(ethylene glycol) bis(p-dimethylaminobenzoate)
1-[4-(2-Hydroxyethoxy)phenyl]-2-hydroxy-2-methyl-1-propane-1-one
1-Butanone, 2-(dimethylamino)-1-[4-(4-morpholinyl) phenyl]-2-(phenylmethyl)-
Phenyl bis(2,4,6-trimethylbenzoyl)phosphine oxide
Benzene, (1-methylethenyl)-, homopolymer, ar-(2-hydroxy-2-methyl-1-oxopropyl)derivs.
2-Hydroxy-4'-(2-hydroxyethoxy)-2-methylpropiophenone
Oxy-phenyl-acetic acid 2-[2-oxo-2-phenyl-acetoxyethoxy]-ethyl ester
Oxy-phenyl-acetic 2-[2-hydroxy-ethoxy]-ethyl ester
Poly[oxy(methyl-12-ethandiyl)],alpha-[4-(di-methylamino)benzoyl-omega-butoxy
2-Hydroxy-1-(4-(4-(2-hydroxy-2-methylpropionyl)benzyl)phenyl-2-methyl-2-propanone
4-(2-hydroxyethoxy)phenyl-(2-hydroxy-2-propyl)ketone
4,4'-Bis(methylethylamino)benzophenone
{a-4-(Dimethylamino)benzoylpoly(oxyethylene)-poly [oxy(1-methylethylene)]-poly(oxyethylene)}4-(dimethylamino)benzoate
1,3-Di({a-2-(phenylcarbonyl)benzoylpoly[oxy(1-methylethylene)]}oxy)-2,2-bis({a-2-(phenylcarbonyl)benzoylpoly[oxy(1-methylethylene)]}oxymethyl)propane 1,3-Di({-4-(dimethylamino)benzoylpoly[oxy(1-methylethylene)]}oxy)-2,2-bis({-4-(dimethylamino)benzoylpoly[oxy(1-methylethylene)]}oxymethyl)propane Poly(oxy-1,2-ethanediyl), a-[2-(4-chlorobenzoyl)benzoyl]-w-[[2-(4-chlorobenzoyl)benzoyl]oxy]-

2-Hydroxy-[4'-(2-Hydroxypropoxy)phenyl]-2-methylpropanone

Polyethylene glycol (200) di(β-4[p-acetylphenyl]piperazine)propionate

Polyethylene glycol (200) di(β-4[4-(2-dimethylamino-2-benzyl)butanoylphenyl]piperazine)propionate.

8. The process according to claim 1, in which the photoactive compound is 2-hydroxy-4'-(2-hydroxyethoxy)-2-methylpropiophenone.

9. The process according to claim 1, in which the photoactive compound (or the mixture of photoactive compounds) is present in the composition in an amount ranging from 0.001% to 20% by weight, relative to the total weight of the composition.

10. The process according to claim 1, in which the applying light radiation is carried out after or at the same time as (simultaneously with) the applying to the skin the cosmetic composition comprising the grafted polysaccharide and the photoactive compound.

11. The process according to claim 1, in which the light radiation is chosen from natural light or artificial light with a wavelength of between 360 and 600 nm.

12. The process according to claim 1, in which the light radiation has at least one of the following characteristics:
    the light radiation has a flux (amount of energy per unit surface area) of between 3 and 100 J/cm$^2$; and/or
    the light radiation is continuous or non-continuous light.

13. The process according to claim 1, in which the light radiation has a source selected from the group consisting of arc lamps; fluorescent lamps; incandescent lamps; LEDs and lasers.

14. The process according to claim 13, in which the exposure time to the light radiation is at least 5 seconds, regardless of the order of the steps (one before the other or simultaneous).

15. The process according to claim 1, wherein the composition is in the form of an O/W emulsion or an aqueous gel.

16. The process according to claim 1, which is intended for attenuating wrinkles.

17. The process according to claim 1, wherein the skin is exposed to the light radiation for at least 5 seconds.

18. The process according to claim 1, wherein the skin is facial skin.

19. The process according to claim 1, wherein the grafted polysaccharide polymer has a degree of grafting ranging from 40% to 70%.

* * * * *